United States Patent
Uhland et al.

(10) Patent No.: US 9,014,799 B2
(45) Date of Patent: Apr. 21, 2015

(54) TRANSMUCOSAL DRUG DELIVERY DEVICE AND METHOD INCLUDING ELECTRICALLY-ACTUATED PERMEATION ENHANCEMENT

(75) Inventors: Scott Uhland, San Jose, CA (US); Eric Peeters, Mountain View, CA (US); Serena Wong, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 880 days.

(21) Appl. No.: 12/576,124

(22) Filed: Oct. 8, 2009

(65) Prior Publication Data

US 2011/0087155 A1    Apr. 14, 2011

(51) Int. Cl.
- *A61N 1/30* (2006.01)
- *A61N 1/32* (2006.01)
- *A61N 1/05* (2006.01)
- *A61N 1/18* (2006.01)

(52) U.S. Cl.
CPC ............... *A61N 1/327* (2013.01); *A61N 1/0512* (2013.01); *A61N 1/0524* (2013.01); *A61N 1/18* (2013.01); *A61N 1/325* (2013.01)

(58) Field of Classification Search
CPC ............. A61M 31/00; A61M 31/002; A61M 2210/1475; A61M 25/0041; A61M 2210/14
USPC ............... 604/20, 891.1, 890.1, 48, 514, 515, 604/93.01, 285
See application file for complete search history.

(56) References Cited

U.S. PATENT DOCUMENTS

| | | |
|---|---|---|
| 4,304,232 A | 12/1981 | Michaels |
| 4,308,867 A | 1/1982 | Roseman et al. |
| 4,402,695 A | 9/1983 | Wong |
| 4,687,423 A | 8/1987 | Maget et al. |
| 4,886,514 A | 12/1989 | Maget |
| 4,902,278 A | 2/1990 | Maget et al. |
| 5,002,540 A | 3/1991 | Brodman et al. |

(Continued)

FOREIGN PATENT DOCUMENTS

| | | |
|---|---|---|
| DE | 4130843 A1 | 3/1993 |
| WO | 94/01165 A1 | 1/1994 |

(Continued)

OTHER PUBLICATIONS

Hashimoto, et al. (2008). "Oxidative stress induces gastric epithelial permeability through claudin-3." Biochemical and Biophysical Research Communications. Retrieved from http://www.elsevier.com//locate/ybbrc. (5 pages).

(Continued)

*Primary Examiner* — Aarti B Berdichevsky
*Assistant Examiner* — Laura Schell
(74) *Attorney, Agent, or Firm* — Sutherland Asbill & Brennan LLP (57) ABSTRACT

Intralumenal devices and methods are provided for transmucosal drug delivery. The device may comprise a housing configured for intralumenal deployment into a human or animal subject; a drug-dispensing portion which contains at least one drug; and an electrically-actuatable portion configured to disrupt at least one region of a mucosal barrier adjacent to the housing at a selected time while intralumenally deployed in the human or animal subject. The device may be operable to dispense the drug from the housing to a region of the mucosal barrier disrupted by the electrically-actuatable portion.

24 Claims, 5 Drawing Sheets

(56) References Cited

U.S. PATENT DOCUMENTS

| | | |
|---|---|---|
| 5,062,834 A | 11/1991 | Gross et al. |
| 5,090,963 A | 2/1992 | Gross et al. |
| 5,112,614 A | 5/1992 | Magruder et al. |
| 5,135,499 A | 8/1992 | Tafani et al. |
| 5,318,557 A | 6/1994 | Gross |
| 5,354,264 A | 10/1994 | Bae et al. |
| 5,415,629 A | 5/1995 | Henley |
| 5,522,804 A | 6/1996 | Lynn |
| 5,593,552 A | 1/1997 | Joshi et al. |
| 5,780,058 A | 7/1998 | Wong et al. |
| 5,816,248 A | 10/1998 | Anderson et al. |
| 5,928,195 A | 7/1999 | Malamud et al. |
| 6,030,375 A | 2/2000 | Anderson et al. |
| 6,086,909 A | 7/2000 | Harrison et al. |
| 6,139,538 A | 10/2000 | Houghton et al. |
| 6,183,434 B1 | 2/2001 | Eppstein |
| 6,322,532 B1 | 11/2001 | D'Sa et al. |
| 6,352,524 B1 | 3/2002 | Bunt et al. |
| 6,423,039 B1 | 7/2002 | Rathbone et al. |
| 6,444,224 B1 | 9/2002 | Rathbone et al. |
| 6,450,991 B1 | 9/2002 | Bunt et al. |
| 6,532,386 B2 | 3/2003 | Sun et al. |
| 6,591,133 B1 | 7/2003 | Joshi |
| 6,638,246 B1 | 10/2003 | Naimark et al. |
| 6,756,053 B2 | 6/2004 | Zhang et al. |
| 6,776,164 B2 | 8/2004 | Bunt et al. |
| 6,805,877 B2 | 10/2004 | Massara et al. |
| 6,835,392 B2 | 12/2004 | Hsu et al. |
| 6,962,579 B2* | 11/2005 | Jellie .................... 604/891.1 |
| 6,978,172 B2 | 12/2005 | Mori et al. |
| 7,004,171 B2 | 2/2006 | Benita et al. |
| 7,083,590 B1 | 8/2006 | Bunt et al. |
| 7,486,989 B2 | 2/2009 | Sun et al. |
| 7,497,855 B2 | 3/2009 | Ausiello et al. |
| 7,732,408 B2 | 6/2010 | Josephson et al. |
| 2002/0010414 A1* | 1/2002 | Coston et al. ............... 604/20 |
| 2003/0018295 A1* | 1/2003 | Henley et al. ............... 604/20 |
| 2003/0130558 A1 | 7/2003 | Massara et al. |
| 2003/0219472 A1 | 11/2003 | Paulelli et al. |
| 2004/0059388 A1 | 3/2004 | Herbst et al. |
| 2004/0082937 A1 | 4/2004 | Ausiello et al. |
| 2004/0087893 A1 | 5/2004 | Kwon |
| 2004/0219192 A1 | 11/2004 | Horstmann et al. |
| 2005/0054969 A1 | 3/2005 | Hoff et al. |
| 2005/0124875 A1 | 6/2005 | Kawano et al. |
| 2005/0244502 A1 | 11/2005 | Mathias et al. |
| 2005/0267440 A1 | 12/2005 | Herman et al. |
| 2006/0024358 A1 | 2/2006 | Santini et al. |
| 2006/0184092 A1 | 8/2006 | Atanasoska et al. |
| 2007/0038181 A1 | 2/2007 | Melamud et al. |
| 2007/0225634 A1 | 9/2007 | Ferren et al. |
| 2007/0269385 A1 | 11/2007 | Yun et al. |
| 2008/0004564 A1 | 1/2008 | Smith |
| 2008/0004596 A1 | 1/2008 | Yun et al. |
| 2008/0262412 A1 | 10/2008 | Atanasoska et al. |
| 2008/0269666 A1 | 10/2008 | Wang et al. |
| 2009/0131737 A1* | 5/2009 | Ferren et al. ............... 600/12 |
| 2009/0171315 A1 | 7/2009 | Versi |
| 2009/0306633 A1 | 12/2009 | Trovato et al. |
| 2011/0087155 A1 | 4/2011 | Uhland et al. |
| 2011/0087192 A1 | 4/2011 | Uhland et al. |
| 2011/0087195 A1 | 4/2011 | Uhland et al. |
| 2013/0211372 A1* | 8/2013 | Rosenshein ............... 604/503 |

FOREIGN PATENT DOCUMENTS

| | | |
|---|---|---|
| WO | 94/18952 A1 | 9/1994 |
| WO | 97/41831 A1 | 11/1997 |
| WO | 01/12101 A1 | 2/2001 |
| WO | 2005/056708 A2 | 5/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009081411 A1 | 7/2009 |
| WO | 2010/048478 A2 | 4/2010 |

OTHER PUBLICATIONS

Seth, et al. (Feb. 21, 2008). "Probiotics ameliorate the hydrogen peroxide-induced epithelial barrier disruption by a PKC- and MAP kinase-dependent mechanism." Am J Physiol Gastrontest Liver Physiol. Retrieved from http://www.ajpgi.org. (10 pages).

EPO Search Report of European Patent Application No. 10187043.4 dated Mar. 3, 2011.

Bridges, et al., "Timed-Artifical Insemination in Beef Cows: What are the Options?," Purdue University Cooperative Extension Service, West Lafayette, IN (REV 3/08).

Sá Filho, O. G. et al., "Fixed-time artificial insemination with estradiol and progesterone for Bos indicus cows II: Strategies and factors affecting fertility," Science Direct, Theriogenology 72 (2009) 210-218.

* cited by examiner

TRANSMUCOSAL DRUG DELIVERY DEVICE AND METHOD INCLUDING ELECTRICALLY-ACTUATED PERMEATION ENHANCEMENT

FIELD

The presently disclosed embodiments relate to implantable medical devices, and more particularly to devices and methods for the transmucosal delivery of drugs to a patient.

BACKGROUND

Transmucosal drug delivery is an area of interest because of the potential of delivering systemically-acting drugs with a high relative bioavailability by avoiding first-pass metabolism effects, the potential of locally delivering therapeutic agents to a site of interest, and the convenience of the application routes. Some of the possible sites for transmucosal drug delivery include the buccal, nasal, vaginal and rectal administration routes.

There are a number of challenges associated with transmucosal drug delivery, particularly with the transmucosal delivery of macromolecules comprising certain amino acid sequences. Enzymes present in fluid secreted by the mucosal tissue degrades certain amino acids. The types of enzymes exhibited by a mucosal tissue vary depending on the location of the mucosal tissue. Enzymes present in the vaginal fluid include nucleases, lysozyme, esterase, guaiacol peroxidase, aldolase, and β-glucuronidase. In addition, aminopeptidase, β-glucuronidase, phosphatases, lactate dehydrogenase, esterases, and type 5 phosphodiesterase are bound to the apical cell layers along the surface of the vaginal mucosa. The presence of these enzymes, particularly the aminopeptidases, is one factor that reduces the bioavailability of vaginally applied protein and peptide drugs.

Other mucosal tissues exhibit other enzymes which may degrade certain drugs. For example, the gastrointestinal tract exhibits mixed function oxidase systems, alcohol dehydrogenase, monoamine oxidase, reductases, p-nitroanisole demethylase, ethoxycournarin-o-deethylase, epoxide hydrolase, UDP-glucuronyltransferase, sulfokinase, glutathione-S-transferase, glycine transferase, acetyltransferase, and calechol-O-methyltransferase. These enzymes reduce the bioavailability of protein and peptide drugs applied to such mucosal tissues.

Furthermore, most mucosal tissues continuously excrete a viscous aqueous-based liquid. This viscous liquid presents additional challenges to transmucosal drug delivery. First, the viscous liquid traps and slows down the intrusion of foreign matter, thus allowing its intrinsic enzymatic and other defense mechanisms time to degrade and/or kill the foreign body. Secondly, the viscous liquid fluid continuously cleans and washes the surface of the mucosal tissue as it is expelled from the tissue. As such, a significant amount of drug may be wasted using conventional application techniques.

In the context of vaginal drug delivery, the vaginal mucosal membrane may be viewed as two barriers in series, an aqueous barrier and the mucosal membrane barrier. The mucosal lining is a stratified squamous epithelium that is glycogenated and nonkeratinized. The human vaginal epithelium consists of approximately 25 cell layers, depending on maturity and location. Like most other stratified epithelia, the human vaginal epithelium contains a tight junction (TJ) system, located in the uppermost cell layers. These TJs separate the apical cell surface domains from the basolateral cell surface domains and provide a primary barrier to the transmucosal delivery of water-soluble species. It is these epithelia and TJs present in all mucosa of the body, not just the vagina, that impede local administration of drug.

Accordingly, it would be desirable to provide devices and methods to improve the effectiveness of transmucosal drug delivery.

SUMMARY

In one aspect, an intralumenal device is provided for transmucosal drug delivery. The device may comprise a housing configured for intralumenal deployment into a human or animal subject; a drug-dispensing portion which contains at least one drug; and an electrically-actuatable portion configured to disrupt at least one region of a mucosal barrier adjacent to the housing at a selected time while intralumenally deployed in the human or animal subject. The device may be operable to dispense the drug from the housing to a region of the mucosal barrier disrupted by the electrically-actuatable portion.

In another aspect, a method is provided for local transmucosal delivery of a drug to a human or animal subject. The method may comprise deploying a drug delivery device within a mucosal tissue lumen, the device comprising a housing and an electrically-actuatable portion; actuating the electrically-actuatable portion to disrupt at least one region of a mucosal barrier adjacent to the housing at a selected time following the insertion; and administering at least one drug through a region of the disrupted mucosal barrier.

In yet another aspect, an intravaginal device is provided for transmucosal drug delivery. The device may comprise a housing configured for intravaginal deployment into a human or animal subject; an electrically-actuatable portion comprising one or more electrically-actuatable active disruption elements configured to disrupt at least one region of a mucosal barrier adjacent to the housing at a selected time while intralumenally inserted into the human or animal subject, and a drug dispenser comprising a drug repository containing at least one drug and a positive displacement element adapted to dispense the at least one drug from the housing into the region of the mucosal tissue disrupted by the electrically-actuatable portion.

DETAILED DESCRIPTION

A transmucosal drug delivery device is provided for intralumenal deployment. The term "intralumenal," as used herein, refers to the placement within a body cavity, channel, tube, or the like, having a mucosal tissue wall. The term includes, but is not limited to, intravaginal, intrauterine, and intragastrointestinal sites. The intralumenal deployment, or placement, of the device is generally maintained for the duration of delivery of at least one or more dosages of the drug. The deployed device may be retrieved from the lumen as desired, including for example, between delivery of individual dosages, following the delivery of several doses of drug, or following completion of a course of treatment of multiple doses. The device may be deployed until the drug payload is depleted.

In some embodiments, the transmucosal drug delivery device includes (i) a housing configured to allow deployment within a lumen, (ii) one or more repositories for containing a drug, and (iii) a plurality of electrically-actuatable active disruption elements for disrupting the mucosal tissue. The drug delivery device may also include an integral control module for controlling the release or delivery of the drug from the device and for actuating the electrically-actuatable active disruption elements.

The active disruption elements may comprise various elements for disrupting the mucosal tissue of the lumen. In some embodiments, the active disruption elements disrupt the mucosal barrier by applying kinetic energy to the mucosal tissue. In certain embodiments, the active disruption elements disrupt the mucosal barrier by applying thermal energy or electromagnetic radiation to the mucosal tissue. In still other embodiments, the active disruption elements disrupt the mucosal barrier by applying electrical energy to the mucosal tissue. The disruption of the mucosal tissue generally renders the tissue more permeable to the drug or otherwise improves the delivery of the drug through the mucosal tissue. For example, the disruption may improve the bioavailability of the drug applied to the mucosal tissue. Various examples of active disruption elements are described in greater detail, hereinafter.

In another aspect, methods are provided for transmucosal drug delivery. The method includes placing, or deploying, the drug delivery device within the lumen of a patient, or a human or animal subject. The lumen may be, for example, a vagina, cervix, uterus, or part of the gastrointestinal tract, such as the rectum.

After the drug delivery device is placed in the lumen, the active disruption elements are electrically actuated to disrupt the mucosal side wall of the lumen. The drug delivery device may then dispense the drug to/through the mucosal tissue in the region of the mucosal tissue disrupted by the active disruption elements. The tissue disruption advantageously can enhance the drug transfer rate and/or amounts able pass undegraded through the mucosal barrier, thereby improving the effectiveness of the transmucosal administration of the drug.

The devices and methods described herein may further include one or more of the mucosal permeation enhancement features and techniques described in U.S. patent application Ser. No. 12/576,087, entitled "Transmucosal Drug Delivery Device and Method Including Chemical Permeation Enhancers" and in U.S. patent application Ser. No. 12/576,075, entitled "Transmucosal Drug Delivery Device and Method Including Microneedles," which are filed concurrently herewith and which are incorporated by reference in their entirety.

Figure 1:
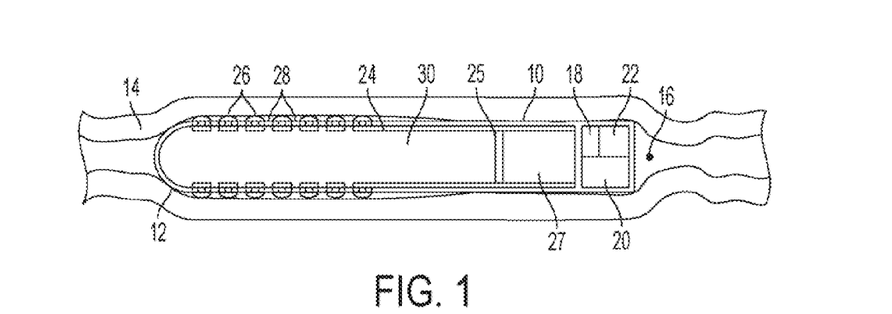
FIG. 1 is a section view, illustrating the placement of a transmucosal drug delivery device in a tissue lumen.
Figure 2:
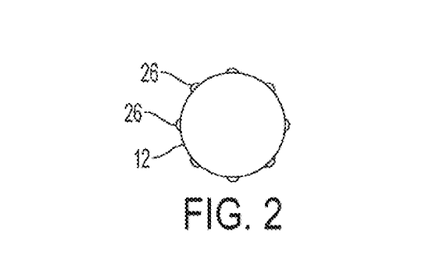
FIG. 2 is an end view, illustrating the transmucosal drug delivery device of FIG.

In some embodiments, the active disruption elements are electrically actuated at a selected time to disrupt the mucosal tissue wall at a selected time while the device is deployed in the lumen. For example, as illustrated in FIG. 1, a transmucosal drug delivery device 10 may be provided having a housing 12 comprising a drug repository 30 containing one or more drugs. The housing 12 may be configured for placement within a lumen 16, having a mucosal tissue 14. The housing 12 may also contain a plurality of active disruption elements 26 provided on the exterior of the housing 12. A plurality of dispensing nozzles 28 may also be provided on the exterior of the housing 12. The drug dispenser may include a piston 25 and an actuator 27 to allow the drug in drug repository 30 to be dispensed by a positive displacement process. The housing 12 may also comprise a control module 18 and a connector 24 for providing an electrical connection between the active disruption elements 26 and the control module 18. The control module 18 may also be electrically connected to the actuator 27 to control the release of the drug from the drug repository 30.

The control module 18 includes a power source 20, such as a battery, and controller 22. The controller 22 may be configured to control the actuation of the active disruption elements 26, and it may control the timing and sequence of the delivery of one or more drugs from the drug repository 30 by actuation of actuator 27. As is described in greater detail hereinafter, various mechanisms may be employed to dispense the drug from the housing via a positive displacement process or otherwise.

Figure 3:
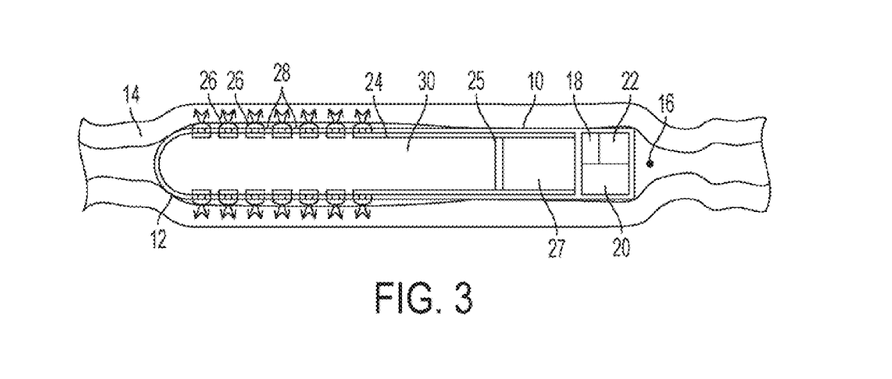
FIG. 3 is a section view, illustrating the active disruption of the mucosal tissue with the active disruption elements of the device of FIG. 1.
Figure 4:
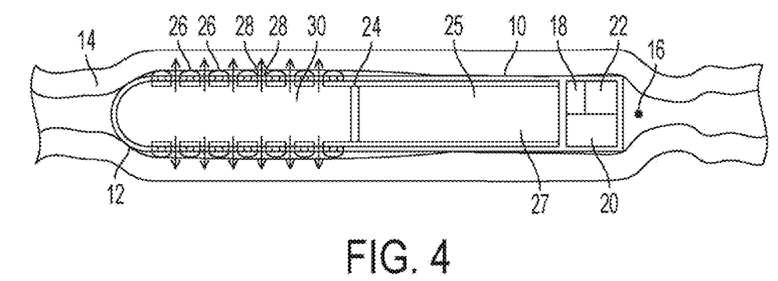
FIG. 4 is a section view, illustrating the delivery of a drug from the device of FIG. 1 into the mucosal tissue after active disruption of the mucosal tissue.

As illustrated in FIG. 3, the actuation of the active disruption elements 26 by the control module 18 may cause the active disruption elements 26 to disrupt the mucosal tissue, such as, for example, by applying thermal or electrical energy into the a region of the mucosal tissue 14 surrounding the device. As illustrated in FIG. 4, once the active disruption elements 26 have disrupted the mucosal tissue 14, the control module 18 may actuate the release of the drug from the drug repository 30 by controlling actuator 27 to advance the piston 25 through the drug repository 30 or the drug may be allowed to diffuse from the device 10 into the mucosal tissue 14 via the dispensing nozzles 28.

Figure 5:
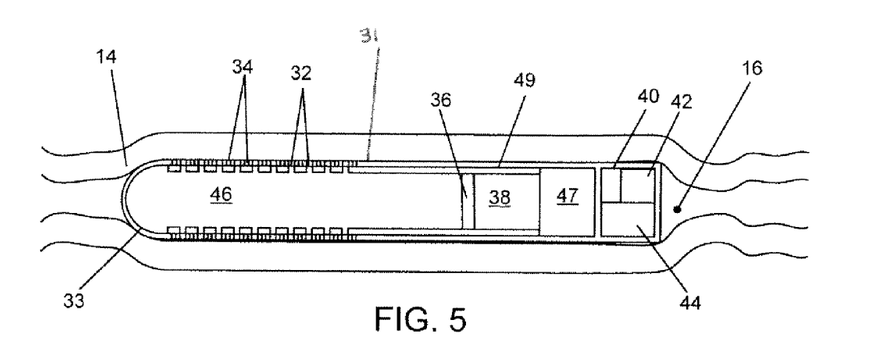
FIG. 5 is a section view, illustrating the placement of a transmucosal drug delivery device in a tissue lumen.

In some embodiments, orifices or nozzles that are fluidly connected with an electrically-actuatable fluid-driving component may be provided in or on the housing. The nozzles or orifices may be employed as active disruption elements for disrupting the mucosal tissue at a selected time by actuation of the fluid-driving component. For example, as illustrated in FIG. 5, a drug delivery device 31 may be provided having a housing containing a drug repository 46, a plurality of orifices or nozzles 34 attached to or integrated with the housing 33, and a manifold 49 fluidly connected with the orifices or nozzles 34. The housing 33 may also comprise a fluid-driving component 47 for applying negative or positive pressure (e.g., delivering a pressurized fluid or suction) to the manifold 49. The housing 33 may also contain a piston 36, an actuator 38 for moving the piston, and a control module 40 for controlling the actuator 38 and/or the fluid driving component 47.

Similar to the embodiment of FIG. 1, the control module 40 of the embodiments of FIG. 5, includes a power source 44, such as a battery, and controller 42. In the embodiment of FIG. 5, the controller 42 may be configured to control the timing of delivery of the drug by controlling actuator 38 and it may control the timing of the actuation of the fluid driving component 47. As is described in greater detail hereinafter, various other mechanisms may be employed to dispense the drug from the housing via a positive displacement process or otherwise.

Figure 6:
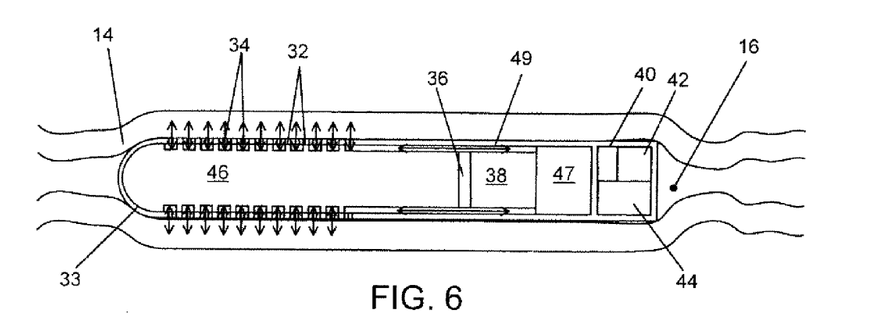
FIG. 6 is a section view, illustrating the active disruption of the mucosal tissue with the vacuum or jet type active disruption elements of the device of FIG. 5.

As illustrated in FIG. 6, once the device is deployed in the lumen, the control module 40 may actuate the fluid driving component 47 to drive a fluid through manifold 49 and the vacuum or jet nozzles 34. The fluid may be a gas or liquid. In some embodiments, the fluid driving component 47 may pull liquids from within the lumen 16 or from the mucosal tissue 14 through the vacuum nozzles 34 and through the manifold 49 and fluid driving component 47. In other embodiments, the fluid driving component 47 may force a fluid through the manifold 49 out the jet nozzles 34 into or against the mucosal tissue 14.

Figure 7:
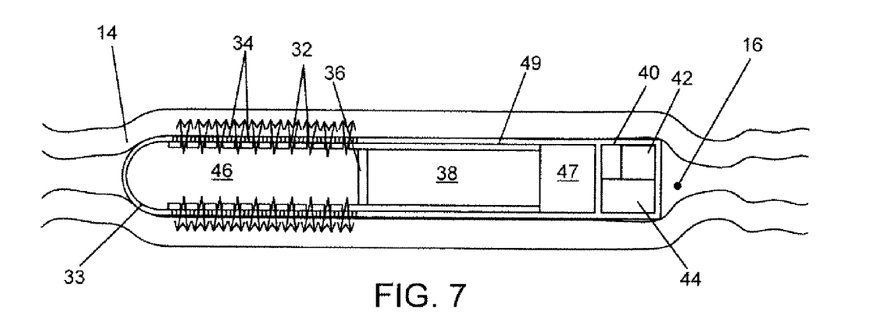
FIG. 7 is a section view, illustrating the delivery of a drug from the device of FIG. 5 into the mucosal tissue after active disruption of the mucosal tissue.

As illustrated in FIG. 7, once the mucosal barrier has been disrupted by the vacuum or jets, the control module 40 may actuate the actuator 38 to advance the piston 36 through the drug repository 46 to dispense the drug from the drug repository 46 through the dispensing nozzles 32 onto the mucosal tissue 14.

Figure 8:
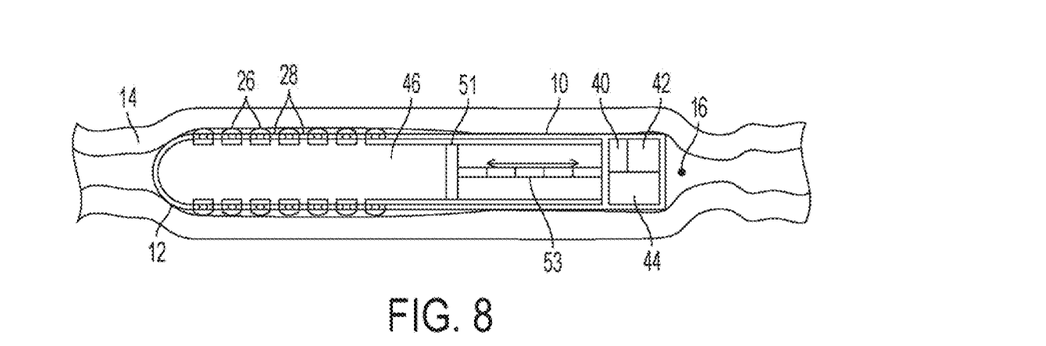
FIG. 8 is a section view, illustrating a drug delivery device having a mechanical displacement mechanism for dispensing a drug from the device.

One or more drugs may be delivered from the device by diffusion or by an active process, such as a positive displacement process. Various positive displacement devices and methods are provided for dispensing the one or more drugs. In some embodiments, a drug may be dispensed from the repository 46 via a mechanical displacement process. For example, as illustrated in FIG. 8, an actuator 53, such as a linear actuator, may extend to advance the piston 51 through the drug repository 46. The control module 40 may provide electrical or mechanical energy to the actuator 53 to control its movement.

Figure 9:
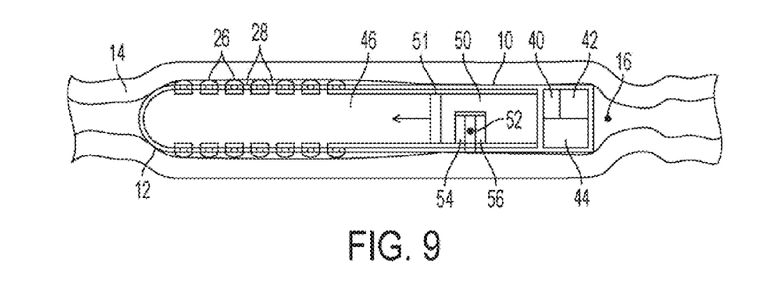
FIG. 9 is a section view, illustrating a drug delivery device having a gas-volume displacement mechanism for dispensing a drug from the device.

In some embodiments, an expandable component may be provided within the housing to cause the drug to dispense when the expandable component expands. For example, as illustrated in FIG. 9, an internal gas-volume displacement pump may be provided in or adjacent to a pump reservoir 50 to actuate the dispensing of the drug contained in drug repository 46 via a positive displacement process. In one embodiment, the pump may include a cathode 54 and anode 56 which contact water or an aqueous solution inside the pump reservoir 50. A channel 52 may be provided in housing to allow aqueous secretions from the mucosal tissue 14 to fill the channel 52 and contact the cathode 54 and anode 56. In other embodiments, a channel 52 that is in fluid communication with the interior space of the lumen 16 may be omitted and electrolytes may be provided on board the device. For example, the pump reservoir 50 may comprise an ionic solution such as sodium nitrate. Alternatively, the pump reservoir 50 may contain deionized water, and a solid electrolyte may be provided in place of the channel 52 so that the solid electrolyte contacts the surfaces of the cathode 54 and anode 56 facing the channel 52. The controller 42 may be configured to control the timing and sequence of delivery of the drug by applying electrical potentials to the cathode 54 and anode 56. A mechanism for generating a gas inside the pump reservoir 50 using the cathode 54 and anode 56 is described in greater detail hereinafter.

Figure 10:
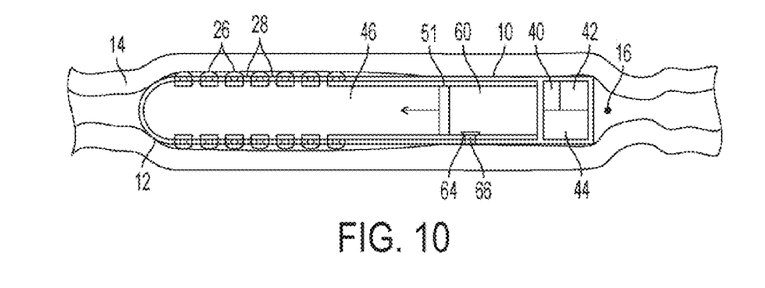
FIG. 10 is a section view, illustrating a drug delivery device having a component enlargement mechanism for dispensing a drug from the device.

In other embodiments, the expandable component may comprise a swellable material or an expandable reservoir. For example, as illustrated in FIG. 10, a swellable material or expandable reservoir 60 may be provided in the housing. A valve 64 may be actuated to allow the ingress of water into the housing via a port 66. In certain embodiments, the expanding component may be a swellable matrix or gel. In other embodiments, the expandable reservoir may contain a phase-transformable material that may change phase from solid or liquid to gas when heat or an electromagnetic field is applied to the material. The controller 42 may be configured to control the timing and sequence of delivery of the drug by actuating a heating source or an electromagnetic field. As is described in greater detail below, various other actuator mechanisms may be used to dispense the drug from the housing via a positive displacement process.

A. Housing

The housing may be generally configured to facilitate deployment of the drug delivery device within a mucosal lumen. In some embodiments, the device may be placed within the lumen by insertion into the lumen via an exterior body orifice. Accordingly, in some embodiments, the housing is shaped and dimensioned to allow insertion and placement, i.e., deployment, of the device within the intended lumen via the exterior body orifice. Specifically, the housing may be shaped and dimensioned for vaginal, cervical, uterine, or rectal insertion and placement. The materials of construction, size, shape, and surface features and other characteristics of the device housing are configured so that the device can be deployed into the mucosal lumen, retained securely in the lumen during operation of the device, and generally retrieved from the lumen following operation of the device or when otherwise desired to be removed. The device configuration is based upon the particular lumenal site and human or animal anatomical considerations, for deployment with minimal discomfort to the patient.

The housing may contain dispensers for dispensing one or more drugs and a control module for controlling the release and delivery of the drugs. The dispensers may include one or more repositories disposed therewithin for containing one or more drugs and one or more nozzles for dispensing the drug out of the housing. The dispenser may be configured to dispense the drug in various directions from the housing. For example, the dispenser may dispense the drug radially out a side wall of the device, axially out of an end of the device, or a combination thereof. The housing may also comprise one or more electrically-actuatable active disruption elements and a control module for actuating the actuating the active disruption elements and the drug dispenser.

The housing may be formed of any biocompatible material. Moreover, the housing material may be resistant to degradation in the environment of the lumen. Examples of suitable materials include stainless steel, titanium, and certain polymers. The material forming the housing may include a coating to enhance biocompatibility and/or operation of the device.

B. Electrically-actuatable Active Disruption Elements

The device may comprise an electrically-actuatable portion, including one or more electrically-actuatable active disruption elements for disrupting the mucosal tissue at a selected time after the device has been deployed into the lumen. The term "at a selected time," when used to refer to the time after the device has been deployed into the lumen that the active disruption elements are actuated, means that the plurality of active disruption elements are electrically actuated after the device is deployed within the lumen for a period of time. This feature may allow the device to be positioned in a desired orientation or location within the lumen before the active disruption elements are actuated.

The electrically-actuatable active disruption elements may be configured to disrupt the mucosal barrier by applying kinetic energy to the mucosal tissue. In some embodiments, the electrically-actuatable active disruption elements are configured to disrupt the mucosal barrier by applying thermal energy to the mucosal tissue. In some embodiments, the electrically-actuatable active disruption elements are configured to disrupt the mucosal barrier by applying electrical energy to the mucosal tissue. Other forms of energy may also be applied to disrupt a region of the mucosal tissue adjacent to the drug delivery device. The disruptions may facilitate the transmucosal delivery of the drug.

Various types of electrically-actuatable active disruption elements may be employed, including, but not limited to, high velocity jets, sound wave transducers, lasers, electrodes, heating elements, vacuum nozzles, or combinations thereof. The electrically-actuatable active disruptions elements may be configured to disrupt the mucosal barrier by various mechanisms, including, but not limited to, electroporation, electrothermal ablation, electrolysis, laser poration, laser ablation, jet penetration, jet cleaning, suction, acoustic disruption or a combination thereof.

As illustrated in FIGS. 1 and 3, a plurality of active disruption elements 26 may be provided on the exterior of the housing 12 of the device 10. The active disruption elements 26 may be electrically actuated at a selected time by the control module 18 which is in electrical communication with the active disruption elements 26 by a connector 24. The connector 24 may be a wiring harness, a circuit board, such as a printed circuit board, or other component suitable for allowing the control module 18 to control the active disruption elements 26. Alternatively, the controller 24 could control the disruption elements 26 wirelessly.

In some embodiments, each active disruption element 26 may comprise a heating element, such as a resistor, for disrupting the mucosal tissue by electrothermal ablation. For example, one or more heating element may apply thermal energy to the mucosal to locally heat regions of the mucosal tissue adjacent to the device. The localized heating of adjacent cells may result in a significant change in their barrier structure, disrupting the cell walls and the junctions which bond cell walls to the cell walls of adjacent cells in epithelial tissue. In some embodiments, cells in a region of the mucosal tissue adjacent to the device may be heated to about 50° C. to about 60° C., or about 55° C., to disrupt the mucosal tissue in the region. Various types of resistive heating elements may be used to heat the adjacent region of the mucosal tissue to the desired temperature.

In some embodiments, each active disruption element 26 may comprise one or more electrodes for disrupting the barrier by electroporation or electrolysis. For example, the control module 18 may be configured to deliver a short voltage shock or pulse to the cells of the mucosal tissue via the electrodes to disrupt the barrier by electroporation. Specific parameters of the pulse, such as duration and voltage, needed to electropermeabilize or disrupt the cell membranes of the mucosal tissue may vary depending on the specific design of the electrode, the environment of the lumen surrounding the electrode, and the level of disruption desired. For example, the electrodes may deliver a pulse of about 10,000 to about 100,000 V/cm lasting about 1 millisecond or less into the cells of the mucosal tissue to disrupt the barrier. In some embodiments, the electrodes and the control module 18 may be configured to disrupt the barrier via electrolysis of the mucosal membrane or degradation of local enzymes.

In other embodiments, a voltage of about 1.3 V or more may be applied within the lumen, resulting in electrolysis of water within the lumen, forming hydrogen and oxygen. The electrolysis may cause the local depletion of water around the mucosal tissue, dehydrating the local area. Local dehydration may lead to locally-reduced enzyme activity and/or increased permeability of the membrane. At significantly higher voltages (e.g., about 10 V or more), the enzymes and/or the membrane itself may participate in electrochemical reactions that lead to localized direct physical disruption.

In some embodiments, each active disruption element 26 may comprise a laser light source or an optic for directing laser light from a laser light source onto the mucosal tissue to disrupt the mucosal barrier by laser poration or laser ablation. In embodiments, where each active disruption element 26 comprises an optic, one or more laser light sources may be directed through a laser splitter or other optics to direct the laser light on the mucosal tissue at sufficient intensity to ablate, porate, or otherwise disrupt the mucosal barrier. The optical disruption of mucosal tissue may utilize photon energy to degrade the molecules within the tissue. In one example, degradation may be accomplished by the absorption of the energy in the proteinaceous molecules, causing dissociation of chemical bonds within the molecules. Alternatively, the energy may be absorbed by water molecules, causing vibration of the water molecules. In the former case, the laser may be configured to provide 7.5 eV to dissociate a C=O bond, 3.6 eV to dissociate a C—O bond, 6.4 eV to dissociate a C=C bond, 3.6 eV to dissociate a C—C bond, 4.8 eV to dissociate a O—H bond, 3.5 eV to dissociate a S—H bond, 4.3 eV to dissociate a C—H bond, 3.0 eV to dissociate a C—N bond, and 4.1 eV to dissociate a N—H bond. The energy of the photons emitted by the laser may be controlled by controlling the wavelength of the light source in accordance with EQ. 1.

$$E(\text{eV}) = \frac{1240}{\lambda(\text{nm})} \qquad \text{EQ. 1}$$

In some embodiments, each active disruption element 26 may comprise a sound transducer for applying acoustic energy to the mucosal tissue to disrupt the mucosal barrier. For example, ultrasonic sound waves may be emitted by the sound transducer at a frequency that may cause disruption of the mucosal tissue. In order to produce disruption of the mucosal tissue via cavitation, the transducer may emit sound in the range of 20-100 kHz. For example, the transducer may emit sound at 20 kHz and 220 mW/cm$^2$ at the transducer surface. Various transducers may be employed, including, but not limited to, sandwich transducers (e.g., longitudinal mode ceramic between plates of metal), flextensional transducers (e.g., ceramic ring with steel plate), flexural transducers (i.e., moonie and cymbal transducers), piezoelectric tube transducers, and electrostatic transducers (e.g., ferroelectric films and capacitive micromachined ultrasonic transducers).

As illustrated in FIGS. 5 and 6, a plurality of orifices or nozzles 34 may be provided on or integrated into the exterior of the housing 33 of the device. The orifices or nozzles 34 may be electrically actuated at a selected time by the control module 40 which controls the fluid driving component 47. The fluid driving component 47 may apply negative or positive pressure into the manifold 49, such as, for example by delivery pressurized fluid or suction into the manifold 49. In embodiments in which the fluid driving component 47 delivers pressurized fluid into the manifold 49, the fluid driving component 47 may comprise a pressurized fluid source and an actuatable valve for delivering the pressurized fluid into the manifold 49. In some embodiments, the fluid driving component 47 may comprise a pump adapted to deliver a pressurized fluid into the manifold 49, and, optionally, one or more intake ports in the housing 33. In embodiments in which the fluid driving component 47 exerts a vacuum force on the manifold 49, the fluid driving component 47 may comprise an evacuated vessel and an actuatable valve for opening the vessel to allow fluids to be drawn into the vessel through the manifold 49. In some embodiments, the fluid driving component 47 may comprise a pump configured to pull fluids through the orifices or nozzles 34 into the manifold 49.

In some embodiments, the fluid driving component 47 provides sufficient driving force to wash away barrier fluids from the surface of the mucosal tissue. In some embodiments, the fluid driving component 47 may provide sufficient driving force to generate a fluid velocity through the orifices or nozzles 34 that allows the fluid to penetrate the mucosal tissue and create diffusive pathways in the mucosal tissue. In either embodiment, the orifices or nozzles 34 and fluid-driving component 47 may be configured to produce fluid flow in the form of a high velocity jet. The fluid of the high velocity jet may be in the form of a gas, a gaseous aerosol, a liquid or a liquid emulsion. In certain embodiments, the drug may be administered substantially simultaneously with the disruption of the mucosal tissue barrier. For example, one or more drugs may be embedded in the fluid that is expelled through the orifices or nozzles 34 such that fluid driving component 47 drives the drug into the mucosal tissue via jet injection.

In some embodiments, the fluid driving component 47 provides sufficient driving force or negative pressure to evacuate the barrier fluids from the surface of the mucosal tissue. The evacuated mucosal fluids may be stored in the device or may be exhausted from the device away from the drug dispensing nozzles 32. In some embodiments, the fluid driving component 47 may provide sufficient vacuum force to leech the tissue, thereby decreasing the diffusion length scale of the mucosal tissue.

C. Drug Dispenser

A drug dispenser may be provided for actively dispensing the drug from the drug delivery device by positive displacement. The drug may be stored in the device in a repository and dispensed from the housing into the lumen or mucosal tissue at a selected time. The drug dispenser may be arranged to dispense the drug from the housing to a region of the mucosal barrier disrupted by the electrically-actuatable active disruption elements.

In some embodiments, the drug may be released from the housing via passive diffusion. In other embodiments, the drug dispenser may employ various positive displacement elements for dispensing the drug from the device including mechanical displacement, osmotic swelling displacement, gas-volume displacement, electrostatically-induced compression, piezoelectric actuation, or a thermally/magnetically induced phase transformation. The positive displacement element may comprise an actuatable dispensing valve in combination with a static pressure head. The term "positive displacement," as used herein, generally refers to any process whereby the drug is dispensed from the drug delivery device under force provided from within the drug delivery device. Accordingly, the term "positive displacement" does not refer to the passive, chemical diffusion of the drug out of the device.

In some embodiments, the drug is stored within a repository within the housing, and is actively dispensed from the housing through a plurality of dispensing nozzles via a mechanical displacement element such as a piston or spring. For example, as illustrated in the embodiment of FIG. 8, the integral control module 40 may selectively transmit electrical or mechanical power to the actuator 53, advancing the piston 51 through the drug repository 46 and dispensing the drug through the dispensing nozzles 28. The actuator 53 may be, for example, a linear actuator that is mechanically or pneumatically driven.

In some embodiments, the drug is dispensed by gas-volume displacement. For example, as illustrated in FIG. 9, the device may include a pump reservoir 50 containing water or an aqueous solution. A pair of electrodes (a cathode 54 and an anode 56) may be provided within the pump reservoir 50 for generating a gas, such as oxygen and hydrogen. A passage 52 may be provided between the electrodes to allow water from within the lumen 16 to exchange protons and electrons with the water or aqueous solution within the pump reservoir 50. In other embodiments, a channel 52 that is in fluid communication with the interior space of the lumen may be omitted and electrolytes may be provided on board the device. For example, the pump reservoir 50 may comprise an ionic solution such as sodium nitrate. Alternatively, the pump reservoir 50 may contain deionized water, and a solid electrolyte may be provided in place of the channel 52 so that the solid electrolyte contacts the surfaces of the cathode 54 and anode 56 facing the channel 52.

An electrical potential of about 1.0 V or greater may be applied to the electrodes to generate $O_2$ at the anode. The reaction at the anode is described by EQ. 2. In the water, at the negatively charged cathode, a reduction reaction takes place, with electrons from the cathode being given to the hydrogen cations to form hydrogen gas as shown in EQ. 3. The pressure exerted by the generated oxygen and hydrogen causes piston 51 to advance into the drug repository 46, thereby causing the drug to dispense through the dispensing nozzles 28 onto the mucosal tissue 14. The production of oxygen and hydrogen may be controlled by an integral control module 40 that is provided on-board the device in the housing. The control module 40 may include a power source 44, such as a battery, and a controller 42 that is programmed to supply the electrical potential to the cathode 54 and the anode 56 at a selected time.

$$2H_2O\ (l) \rightarrow O_2\ (g) + 4H^+\ (aq) + 4e^- \quad\quad\quad EQ.\ 2$$

$$2H^+\ (aq) + 2e^- \rightarrow H_2\ (g) \quad\quad\quad EQ.\ 3$$

Other positive displacement elements may be better understood with reference to FIG. 10. In these examples, a drug contained in a drug repository 46 is dispensed by the enlargement of component 60. Component 60 may be, for example, a swellable material (such as a swellable gel) or an expandable reservoir. In some embodiments, the drug is dispensed by osmotic swelling displacement. Optionally, a valve 64 may be provided to selectively control the ingress of water into the repository or swellable material through a port 66 or a semipermeable membrane. Water from the lumen 16 may be drawn into a repository or swellable material, causing the repository or swellable material to expand in volume. The expansion of the reservoir or swellable material may displace a volume of drug contained within the housing, causing the drug to be dispensed from the device into the mucosal tissue 14. The actuation of the valve 64 may be controlled by the integral control module 40.

In other embodiments, the drug may be dispensed by an expansive force supplied by an induced phase transformation. For example, component 60 may comprise an expandable reservoir containing a phase-transformable material. The phase-transformable material may be any liquid or solid that will undergo a phase transition from solid or liquid to gas when heated or subjected to an electromagnetic field. When the material transforms to a gas, the material expands and advances through the drug repository 46 to dispense the drug from the device. The actuation of the phase-transformation may be controlled by the on-board control module 40.

In other embodiments, the drug may be positively displaced and dispensed from the housing by electrostatically-induced compression or using a piezoelectric actuator. For example, a dielectric elastomeric actuator or piezoelectric actuator may be arranged such that a change in voltage or current to the actuator causes the actuator to exert a compressive force on the drug in the drug repository. This compressive force may cause the drug to be dispensed from the device. The actuation of the actuator may be controlled by the on-board control module.

In other embodiments, positive displacement of the drug may be achieved using a static pressure head and an actuatable valve. The valve may be operated, for example, in an analog mode for amplitude-modulated dosing or it may be operated in a digital mode for frequency/duty-cycle modulated dosing. The static head pressure may be provided by loading the drug into the device under pressure or the device may be pressurized after the drug is loaded in the device.

In various embodiments, the device may be configured for wireless operation, e.g., following deployment in the human or animal subject. In such cases, the device includes appropriate telemetry components as known in the art. For example, actuation of the mucosal barrier disruption and/or the drug dispensing may be done from a remote controller, e.g., external to the human or animal subject. Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if stored, a storage device, such as a rechargeable battery or capacitor. In still another case, the device is both wirelessly powered and wirelessly controlled.

Drugs

Various drugs may be administered from the drug delivery device. The drug may be a protein or a peptide. For example, in some embodiments, the drug delivery device may be used to administer hormones or steroids, including, but not limited to, follicle stimulating hormone, parathyroid hormone, luteinizing hormone, gonadotropin-releasing hormone (GnRH), estradiol, progesterone, melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, atrial-natriuretic peptide, calcitonin, cholecystokinin, corticotropin-releasing hormone, erythropoietin, gastrin, ghrelin, glucagon, growth hormone-releasing hormone, human chorionic gonadotropin, human placental lactogen, growth hormone, inhibin, insulin, insulin-like growth factor, leptin, melanocyte stimulating hormone, orexin, oxytocin, prolactin, relaxin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estrone, estriol, calcitriol, calcidiol, prostaglandins, leukotrienes, prostacyclin, thromboxane, prolactin releasing hormone, lipotropin, brain natriuretic peptide, neuropeptide Y, histamine, endothelin, enkephalin, renin, and pancreatic polypeptide.

In some embodiments, the drug delivery device may be used to administer cytokine signaling molecules or immunomodulating agents that are used in cellular communication. These molecules commonly comprise proteins, peptides, or glycoproteins. Cytokine signaling molecules include, for example, the four α-helix bundle family which include the IL-2 subfamily (e.g., erythropoietin (EPO) and thrombopoietin (THPO)), the interferon (IFN) subfamily and the IL-10 subfamily. Cytokine signaling molecules also include the IL-1, IL-18 and IL-17 families.

In some embodiments, the drug delivery device may be used to administer drugs for pain management, including, but not limited to, corticosteroids, opioids, antidepressants, anticonvulsants (antiseizure medications), non-steroidal anti-inflammatory drugs, COX2 inhibitors (e.g., rofecoxib and celecoxib), tricyclic antidepressants (e.g., amitriptyline), carbamazepine, gabapentin and pregabalin, codeine, oxycodone, hydrocodone, diamorphine, and pethidine.

In some embodiments, the drug delivery device may be used to administer cardiovascular drugs. Examples of cardiovascular drugs that may be administered with the device include B-type natriuretic peptide (BNP), atrial natriuretic peptide (ANP), atrial natriuretic factor (ANF), atrial natriuretic hormone (ANH), and atriopeptin. Cardiovascular drugs that may be administered by the device also include, for example, antiarrhythmic agents, such as Type I (sodium channel blockers), including quinidine, lidocaine, phenytoin, propafenone; Type II (beta blockers), including metoprolol; Type III (potassium channel blockers), including amiodarone, dofetilide, sotalol; Type IV (slow calcium channel blockers), including diltiazem, verapamil; Type V (cardiac glycosides), including adenosine and digoxin. Other cardiacvascular drugs that may be administered by the device include ACE inhibitors, such as, for example, captopril, enalapril, perindopril, ramipril; angiotensin II receptor antagonists, such as, for example, candesartan, eprosartan, irbesartan, losartan, telmisartan, valsartan; beta blocker; and calcium channel blocker.

The drug may be formulated with one or more pharmaceutically acceptable excipients as needed to facilitate the drug's storage in and release from the device. In one embodiment, the drug may be in a liquid solution or suspension. The drug may be in the form of microparticles or nanoparticles. The solvent or carrier may be aqueous or organic.

D. Control Module

A control module is provided for electrically actuating the active disruption elements and/or the delivery of the drug into the mucosal tissue. The control module may be provided on-board the drug delivery device in the housing. The control module may include a power source and a controller. The power source may be any source of mechanical or electrical power, such as a battery or fuel cell. The controller may be programmable, or it may be pre-programmed to deliver the drug in accordance and/or actuate the active disruption elements with a pre-designated schedule.

In some embodiments, the control module may further comprise one or more sensors for analyzing the environment around the device or within the lumen. For example, a sensor may be employed to detect the presence of a hormone or other substance in the body, such as in the mucosal lumen in which the device is deployed.

In some embodiments, the control module may further comprise a wireless receiver for receiving wireless control signals from a separate, detached transmitting device. In certain embodiments, the device may be deployed into the lumen by the patient or a physician, and, thereafter, the patient or physician may actuate the release of the drug using the transmitting device to transmit control signals to the placed device. Furthermore, in some embodiments, the control module receiver and transmitting device may both be transceivers capable of transmitting and receiving control signals and other communications from each other. Accordingly, in certain embodiments, the control module transceiver may transmit data relevant to the operation of the device, such as data regarding the dosages already administered, the dosing schedule, the level of drug remaining in the repositories, and the remaining battery charge, as well as data relevant to the environment of the lumen, such as data detected or measured by an integral sensor. In some embodiments, the control module may also be wirelessly powered.

E. Methods

Methods are provided for transmucosal drug delivery using intralumenal devices. The method includes deploying the drug delivery device within the lumen of a patient. The patient may be a human or other mammalian animal (e.g., cow, horse, pig, or dog). The methods include various medical and veterinary therapies, as well as animal husbandry applications. The lumen may be, for example, a vagina, cervix, uterus, bladder, or rectum. The device may be adapted to contact essentially any mucosal tissue surface. The device may be placed in the lumen by inserting the device through an exterior orifice of the patient into the lumen. In some embodiments, the device may be in a form that may be orally administered for delivery of a drug via the mucosal tissue of the gastrointestinal tract.

After the drug delivery device is placed in the lumen, the active disruption elements are electrically actuated to disrupt the mucosal side wall. In some embodiments, the active disruption elements may be actuated to disrupt the mucosal tissue by an integral control module at a selected time. The drug delivery device may then dispense the drug to a region of the mucosal tissue disrupted by the active disruption elements. The release of the drug from the device may also be actuated by the control module at another selected time after the active disruption elements have disrupted the mucosal tissue.

As illustrated in FIG. 1, the transmucosal drug delivery device 10 may be deployed in a lumen 16. The drug delivery device 10 may be held in place by frictional engagement between the mucosal tissue 14 and the housing 12. As illustrated in FIG. 3, the active disruption elements 28 may then be actuated to extend disrupt the mucosal tissue 14. The actuation of the active disruption elements 26 may be controlled by the control module 18. In some embodiments, as illustrated in FIGS. 5 and 6, a drug delivery device may be placed in the lumen 16, and the jet or vacuum nozzles 34 may be actuated to disrupt the mucosal tissue 14.

After disruption of the mucosal tissue 14, the control module 40 may actuate the delivery of the drug. In the example of FIG. 8, the control module 40 may supply electrical or mechanical energy to actuator 53. In the example of FIG. 9, the control module 40 may apply an electrical potential to the cathode 54 and the anode 56. As gas is generated within the pump reservoir 50, the piston 58 advances through the drug repository 46, causing the drug to be dispensed through the dispensing nozzles 28. In embodiments in which a swellable material or enlargeable repository is used such as the embodiment of FIG. 10, the valve 64 may be actuated to allow the ingress of water into the swellable material or expandable reservoir 60. Alternatively, the control module 40 may actuate the inducement of a phase change of a material in the expandable reservoir 60. For example, the control module 40 may actuate a heating element to heat the phase change material or may actuate a circuit that generates an electro-magnetic field. The enlargement of the swellable material or expandable reservoir 60 forces the drug out of the dispensing nozzles 28 and onto the mucosal tissue 14.

Applications

The drug delivery device and method may be used for various therapeutic applications. In some embodiments, the drug delivery device may be used to treat infertility in a female subject. For example, the drug delivery device may be placed in the vagina (or uterus, or other part of the birth canal) of a female subject. The active disruption elements may then be electrically-actuated to disrupt the mucosal barrier. Thereafter, the drug delivery device may deliver follicle stimulating hormone to induce ovulation in the female subject. In some embodiments, the drug delivery device may be configured to deliver a plurality of hormones, including follicle stimulating hormone, luteinizing hormone, gonadotropin-releasing hormone separately, or in combination, in appropriate sequences, at appropriate times, and in appropriate amounts to treat infertility. The device may also dispense estradiol to regulate natural hormone production in the female subject. The appropriate dosing schedule and amounts may be determined by one in the field of reproductive pharmacology.

In another embodiment, the drug delivery device may be use to treat insulin dependent diabetes (Type I diabetes) in a subject. The drug delivery device may be placed within a lumen of the subject. The active disruption elements may then be electrically-actuated to disrupt the mucosal barrier. Thereafter, the drug delivery device may deliver insulin (Humulin R, Novolin R), insulin isophane (Humulin N, Novolin N), insulin lispro (Humalog), insulin aspart (NovoLog), insulin glargine (Lantus) or insulin detemir (Levemir) to the patient at a selected time or times.

In another embodiment, the drug delivery device may be use to treat diabetes mellitus (Type II diabetes) in a subject. The drug delivery device may be placed within a lumen of the subject. The active disruption elements may then be electrically-actuated to disrupt the mucosal barrier. Thereafter, the drug delivery device may deliver exenatide to the patient at a selected time or times.

In another embodiment, the drug delivery device may be use to treat breast or ovarian cancer in a subject. The drug delivery device may be placed within a lumen of the subject, such as the vagina for a female subject. The active disruption elements may then be electrically-actuated to disrupt the mucosal barrier. Thereafter, the drug delivery device may deliver abraxane (or another drug effective in the treatment of cancer) to the patient at a selected time or times.

In another embodiment, the drug delivery device may be use to treat HIV/AIDS in a subject. The drug delivery device may be placed within a lumen of the subject. The active disruption elements may then be electrically actuated to disrupt the mucosal barrier. Thereafter, the drug delivery device may deliver Abacavir (ABC) or Cidofovir (or another drug effective in the treatment of HIV/AIDS) to the patient at a selected time or times. The device also may be used to treat other sexually transmitted diseases.

In another embodiment, the drug delivery device may be use to treat genital herpes in a subject. The drug delivery device may be placed within a lumen of the subject, such as within the vagina of a female subject. The active disruption elements may then be electrically actuated to disrupt the mucosal barrier. Thereafter, the drug delivery device may deliver acyclovir, famciclovir, or valacyclovir (or another drug effective in the treatment of genital herpes) to the patient at a selected time or times.

In another embodiment, the drug delivery device may be use to treat diabetes insipidus in a subject. The drug delivery device may be placed within a lumen of the subject. The active disruption elements may then be electrically actuated to disrupt the mucosal barrier. Thereafter, the drug delivery device may deliver desmopressin (or another drug effective in the treatment of diabetes insipidus) to the patient at a selected time or times.

In another embodiment, the drug delivery device may be use to treat osteoporosis in a subject. The drug delivery device may be placed within a lumen of the subject, such as within the vagina of a female subject. The active disruption elements may then be electrically-actuated to disrupt the mucosal barrier. Thereafter, the drug delivery device may deliver ibandronate, calcitonin, or parathyroid hormone (or another drug effective in the treatment of osteoporosis) to the patient at a selected time or times.

It will be appreciated that various of the above-disclosed and other feature and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

We claim:

1. An intravaginal device for transmucosal drug delivery comprising:
    a housing shaped and dimensioned for intravaginal deployment and for holding the device in place in the vagina by frictional engagement between the housing and mucosal tissue of a human or animal subject;
    a drug-dispensing portion comprising a piston, an actuator, and a drug repository which contains at least one drug;
    an electrically-actuatable portion comprising a plurality of electrically-actuatable active disruption elements configured to disrupt at least one region of a mucosal barrier adjacent to the housing at a selected time while intravaginally deployed and retained in the human or animal subject; and
    a control module contained in the housing, the control module controlling the active disruption elements and the timing and sequence of the delivery of the drug from the drug repository by activation of the actuator and piston,
    wherein the device is operable to dispense the drug from the housing to a region of the mucosal barrier disrupted by the electrically-actuatable portion.

2. The device of claim 1, wherein the drug comprises a protein or peptide.

3. The device of claim 1, wherein the drug comprises a hormone or steroid.

4. The device of claim 1, further comprising a receiver adapted to receive power or control signals from a transmitting device when the device is intralumenally deployed.

5. The device of claim 1, wherein the actuator comprises a mechanical displacement element, an osmotic swelling displacement element, a gas-volume displacement element, a magnetically-induced phase transformation element, a thermally-induced phase transformation element, a piezoelectric actuator, or an electrostatically-induced compression element.

6. The device of claim 1, wherein the electrically-actuatable active disruption elements are configured to disrupt the mucosal barrier by applying kinetic energy to the mucosal tissue.

7. The device of claim 1, wherein the electrically-actuatable active disruption elements are configured to disrupt the mucosal barrier by applying thermal energy or electromagnetic radiation to the mucosal tissue.

8. The device of claim 1, wherein the electrically-actuatable active disruption elements are configured to disrupt the mucosal barrier by applying electrical energy to the mucosal tissue.

9. The device of claim 1, wherein the electrically-actuatable active disruption elements are configured to disrupt the mucosal barrier by electroporation, electrothermal ablation, electrolysis, laser poration, laser ablation, jet penetration, jet cleaning, suction, acoustic disruption or a combination thereof.

10. The device of claim 1, wherein the electrically-actuatable active disruption elements are selected from the group consisting of a high velocity jet, a sound wave transducer, a laser, an electrode, a heating element, a vacuum nozzle, and a combination thereof.

11. A method for local transmucosal delivery of a drug to a human or animal subject comprising:
    deploying and retaining a drug delivery device within a vagina of the human or animal subject, the device comprising a housing configured for holding the device in place in the vagina by frictional engagement with mucosal tissue and an electrically-actuatable portion;
    actuating the electrically-actuatable portion to disrupt at least one region of a mucosal barrier adjacent to the housing at a selected time following the deployment; and then after the mucosal barrier has been disrupted,
    driving a piston in the housing to mechanically displace a drug from a reservoir in the housing, to thereby dispense the drug from the housing to a region of the disrupted mucosal barrier.

12. The method of claim 11, wherein the drug comprises a protein or peptide.

13. The method of claim 11, wherein the process of driving the piston comprises mechanical displacement, osmotic swelling displacement, gas-volume displacement, magnetically-induced phase transformation, thermally-induced phase transformation, piezoelectric actuation, or electrostatically-induced compression.

14. The method of claim 11, wherein the electrically-actuatable portion comprises one or more electrically-actuatable active disruption elements selected from the group consisting of a high velocity jet, a sound wave transducer, a laser, an electrode, a heating element, a vacuum nozzle, and a combination thereof.

15. The method of claim 11, wherein the step of actuating the electrically-actuatable portion comprise disrupting the mucosal barrier by electroporation, electrothermal ablation, electrolysis, laser poration, laser ablation, jet penetration, jet cleaning, suction, acoustic disruption or a combination thereof.

16. An intravaginal device for transmucosal drug delivery comprising:
    a cylindrical housing configured for intravaginal deployment into and retention in a human or animal subject;
    an electrically-actuatable portion comprising one or more electrically-actuatable active disruption elements configured to disrupt at least one region of a mucosal barrier adjacent to the housing at a selected time while deployed and retained in the vagina of the human or animal subject;
    a drug dispenser comprising a drug repository containing at least one drug and a piston operable to dispense the at least one drug from the repository through a plurality of orifices or nozzles in the housing and in fluid communication with the repository into the region of the mucosal tissue disrupted by the electrically-actuatable portion; and a control module contained in the housing, the control module controlling the active disruption elements and the timing and sequence of the delivery of the drug from the drug repository by activation of an acutator for the piston.

17. The device of claim 16, wherein the actuator comprises a mechanical displacement element, an osmotic swelling displacement element, a gas-volume displacement element, a magnetically-induced phase transformation element, a thermally-induced phase transformation element, or a combination thereof.

18. The device of claim 16, wherein the drug comprises a protein or peptide.

19. The device of claim 16, wherein the one or more electrically-actuatable active disruption elements are selected from the group consisting of a high velocity jet, a sound wave transducer, a laser, an electrode, a heating element, a vacuum nozzle, and a combination thereof.

20. The device of claim 16, wherein the electrically-actuatable active disruption elements are configured to disrupt the mucosal barrier by electroporation, electrothermal ablation, electrolysis, laser poration, laser ablation, jet penetration, jet cleaning, suction, acoustic disruption, or a combination thereof.

21. The device of claim 16, wherein the electrically-actuatable portion and the drug dispenser are cooperatively configured to administer the at least one drug after the disruption of the mucosal tissue barrier.

22. An intravaginal device for transmucosal drug delivery comprising:

a cylindrical housing shaped and dimensioned for intravaginal deployment and for holding the device in place in the vagina by frictional engagement between the housing and mucosal tissue of a human or animal subject, the housing having a plurality of dispensing nozzles;

an electrically-actuatable portion comprising one or more electrically-actuatable active disruption elements configured to disrupt at least one region of a mucosal barrier adjacent to the housing at a selected time while deployed and retained in the vagina of the human or animal subject, and a drug dispenser comprising
a drug repository containing at least one drug, the drug repository being located in the axial center of the housing in fluid communication with the plurality of dispensing nozzles, and
a positive displacement element adapted to apply a mechanical force to the at least one drug to dispense the at least one drug from the plurality of dispensing nozzles into the region of the mucosal tissue disrupted by the electrically-actuatable portion.

23. The intravaginal device of claim 22, wherein the plurality of nozzles dispense the drug radially in at least two opposed directions from a sidewall of the cylindrical housing.

24. The intravaginal device of claim 22, wherein the positive displacement element comprises a piston and an actuator operably associated with the piston.

* * * * *